(12) United States Patent
Gidon

(10) Patent No.: US 9,411,102 B2
(45) Date of Patent: Aug. 9, 2016

(54) DEVICE FOR EMITTING AND GUIDING AN INFRARED RADIATION

(75) Inventor: Serge Gidon, La Murette (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 42 days.

(21) Appl. No.: 14/112,707

(22) PCT Filed: Apr. 18, 2012

(86) PCT No.: PCT/IB2012/051947
§ 371 (c)(1),
(2), (4) Date: Oct. 18, 2013

(87) PCT Pub. No.: WO2012/143869
PCT Pub. Date: Oct. 26, 2012

(65) Prior Publication Data
US 2014/0054460 A1 Feb. 27, 2014

(30) Foreign Application Priority Data

Apr. 19, 2011 (FR) ...................... 11 53380

(51) Int. Cl.
*G01J 5/00* (2006.01)
*G02B 6/10* (2006.01)
*G02B 6/26* (2006.01)
*G01N 21/3504* (2014.01)
*G01N 33/00* (2006.01)
*G01N 21/17* (2006.01)

(52) U.S. Cl.
CPC ............. *G02B 6/26* (2013.01); *G01N 21/3504* (2013.01); *G01N 33/0009* (2013.01); *G02B 6/102* (2013.01); *G01N 21/1702* (2013.01)

(58) Field of Classification Search
CPC ............. G01J 5/00; G01N 21/61; G02B 6/10; G02B 6/12
See application file for complete search history.

(56) References Cited

U.S. PATENT DOCUMENTS

| | | | |
|---|---|---|---|
| 5,834,777 A * | 11/1998 | Wong | 250/343 |
| 7,418,166 B1 | 8/2008 | Kapur et al. | |
| 2007/0120057 A1 | 5/2007 | Tsai et al. | |
| 2011/0073875 A1 | 3/2011 | Griebenow et al. | |
| 2011/0174799 A1* | 7/2011 | Ali et al. | 219/446.1 |
| 2012/0267532 A1* | 10/2012 | Udrea et al. | 250/338.5 |
| 2014/0291704 A1* | 10/2014 | Ali et al. | 257/88 |

FOREIGN PATENT DOCUMENTS

WO WO-00/04616 A1 1/2000

OTHER PUBLICATIONS

Kasberger, J., et al.; "*Grating-Coupling of Thermal Radiation as an Essential Element of a Fully Integrated IR-Absorption Sensor System;*" Proceedings Sensor + Test 2008; pp. 161-166; dated 2008; abstract retrieved on Nov. 21, 2013 from <http://www.jku.at/content/e263/e16099/e16086/e173791/?view=PUBD&feid=268&pub_id=27808>.

International Search Report and Written Opinion for Application No. PCT/IB2012/051947; dated Jul. 11, 2012.

\* cited by examiner

*Primary Examiner* — Casey Bryant
(74) *Attorney, Agent, or Firm* — Alston & Bird LLP

(57) ABSTRACT

Device for emitting and guiding an infrared radiation comprising a waveguide (1) and means (5) for emitting an infrared radiation (R), characterized in that said means (5) for emitting an infrared radiation (R) are formed at the surface or inside the waveguide (1), in such a way that the radiation emitted is transmitted to the waveguide (1) which transports it.

10 Claims, 3 Drawing Sheets

DEVICE FOR EMITTING AND GUIDING AN INFRARED RADIATION

FIELD

The present invention relates to a device for emitting and for guiding infrared radiation.

BACKGROUND

Devices of this type have already been proposed. Generally speaking, they comprise a waveguide and means for emitting infrared radiation.

The main difficulty of these devices is to ensure an efficient coupling between the waveguide and the emission means.

The article by J. Kasberger and B. Jakoby, "Grating-coupling of thermal radiation as an essential element of a fully integrated IR-absorption sensor system" may thus be cited, which appeared in OPTO Conference 2008 Proceedings, pages 161 and following.

This article describes a sensor whose operation is based on infrared absorption in the evanescent field region of a waveguide using thermally generated infrared radiation. The coupling between the thermal radiator emitting the infrared radiation and the waveguide is achieved by means of a network coupler.

However, the efficiency of the coupling obtained remains modest.

It should furthermore be noted that some solutions, known in the field of macroscopic optics, cannot be transposed to waveguides.

Thus, notably in photo-acoustics, thermal sources may be implemented in the form of filaments. However, they cannot be used with a waveguide owing to their high divergence.

For this reason, the solution which is widely adopted consists in coupling the waveguide to a laser source. Thus, laser sources have already been fabricated based on complex semiconductor structures.

They do however remain difficult to control and, to this today, their energy efficiency is fairly low, since it is of the order of 1/1,000.

SUMMARY

The object of the invention is to overcome these drawbacks by providing a device for emitting and for guiding infrared radiation that guarantees an efficient coupling between the waveguide and the means for emitting infrared radiation.

According to the invention, this device is characterized in that said means for emitting infrared radiation can be formed on the surface or inside of the waveguide.

The presence of the emission means on the surface or inside of the waveguide allows an efficient transmission of infrared radiation into the waveguide which subsequently transports it.

Preferably, the means for emitting infrared radiation comprise means of emission of heat and means capable of emitting infrared radiation under the effect of the emitted heat.

The means of emission of heat can be resistive means capable of emitting heat by resistive heating.

In one particular embodiment, the means for emitting infrared radiation comprise a resistive track made from an electrically conductive material, which is designed to be connected to an electrical current supply source in order to emit heat, and an emissive layer made of a material capable of emitting infrared radiation under the effect of heat, said emissive layer being placed between the waveguide and the conducting track.

Furthermore, the means for emitting infrared radiation are preferably in direct contact with the waveguide, in such a manner as to increase the efficiency of the transmission of the infrared radiation within the waveguide.

Preferably, the waveguide is at least partially surrounded by a thermal insulator.

This allows the efficiency of the transmission of the infrared radiation inside the waveguide to be further increased.

Advantageously, the means for emitting infrared radiation comprise an interface layer in contact with the waveguide.

In a preferred embodiment, the means for emitting infrared radiation extend over or within at least a part of the waveguide.

In a first variant embodiment, this part is supported at its proximal end, its distal end being free. The distal end is referred to as 'free' in the sense that it is not supported by a support layer; it is suspended inside a cavity.

In a second variant embodiment, the proximal and distal ends of said part are supported, a cavity being formed between these two ends.

In one preferred embodiment, the conducting track has a narrower width near to the distal end of said part than in the rest of the waveguide.

Advantageously, the conducting track exhibits a tapered shape in the direction of this distal end.

The invention also relates to a gas detector comprising a device for emitting and for guiding infrared radiation, according to the invention.

BRIEF DESCRIPTION OF THE DRAWINGS

Other features and advantages of the invention will become more clearly apparent upon reading the description that follows and which is presented with regard to the appended drawings, in which.

DETAILED DESCRIPTION

The elements common to the various figures will be denoted by the same references.

Figure 1:
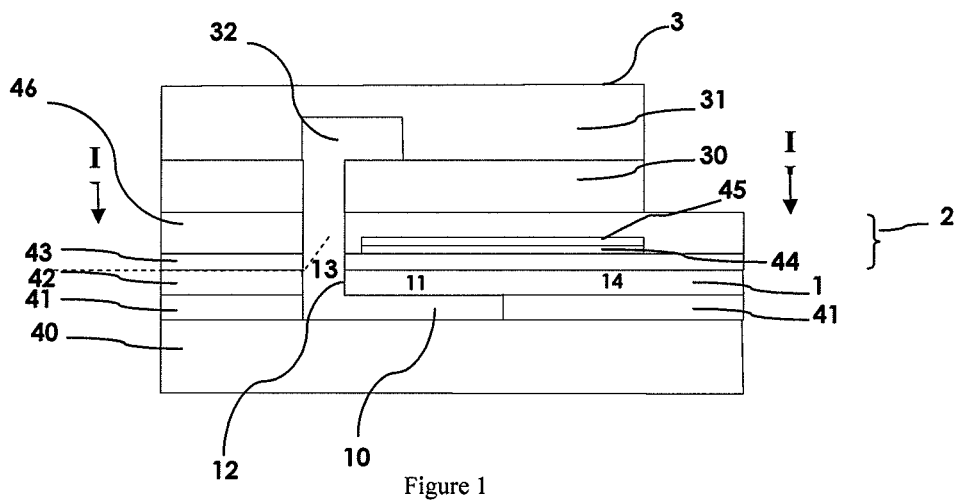
FIG. 1 is a schematic view of a transverse cross section of one example of an emission and guiding device according to the invention.

FIG. 1 illustrates one exemplary embodiment of an emission and guiding device according to the invention.

This device comprises a waveguide 1 on which means 2 for emitting infrared radiation and a cover 3 are provided.

Figure 2:
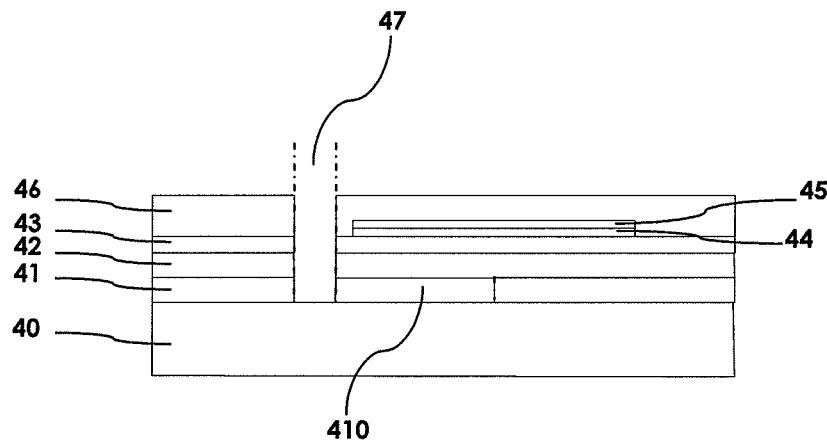
FIG. 2 shows an intermediate step in the method for obtaining the device illustrated in FIG. 1, FIGS. 3 to 5 are top views of the device illustrated in FIG. 1, in the plane I-I, these figures illustrating several variant embodiments for the means for emitting infrared radiation.

FIG. 2 more particularly illustrates a multilayer starting from which the waveguide and the means for emitting infrared radiation are obtained.

In the example illustrated, this multilayer first of all comprises three layers: a substrate layer 40 which is for example made of silicon, a layer 41 for example of silica and a layer 42 for example of silicon and, preferably, of SiGe on silicon.

The layers 40 and 41 will form the support for the waveguide.

Generally speaking, the thickness of the support layer 41 is relatively large in order to avoid losses by evanescent coupling at the useful wavelength, in other words over the wavelength range around the absorption line of the gas. By way of example, for an absorption line of 4.2 µm, the range included is between 4.1 and 4.3 µm.

By way of example, the thickness of the support layer of silica 41 will be of at least 1 µm for a useful wavelength of around 4 µm.

The thickness of the layer of silicon 42 could be in the range between 600 nm and several micrometers.

The thickness of the substrate layer of silicon 40 is greater than 80 µm.

An interface layer 43 is deposited on the layer 42.

This layer may be formed from various materials, notably $SiO_2$ or $Si_3N_4$, its thickness being of the order of a fraction of the useful wavelength ($\lambda$), for example $\lambda/10$.

Furthermore, this layer is optional. Its function will be explained in the following part of the description.

Over a part of the stack of the four layers 40 to 43, a layer 44 of a material with a high thermal emissivity is subsequently deposited.

This emissive layer 44 has a thermal emissivity, also referred to as emissivity coefficient, greater than 0.5, preferably greater than 0.7, and advantageously greater than 0.9.

The term "emissive layer" denotes a layer capable of emitting infrared radiation designed to be transmitted within the waveguide.

This emissive layer 44 can notably be a layer of TiN.

A resistive layer 45 of an electrically conductive material is formed on this emissive layer 44.

In one variant embodiment, the emissive layer 44 is formed over the entire surface of the multilayer and it is subsequently etched so as to only subsist over a part of the multilayer.

The resistive layer 45 may also be formed over the whole surface of the multilayer then etched with the emissive layer 44.

This layer 45 can notably by a layer of Pt.

The structuring of the resistive layer 45 is then carried out in such a manner as to obtain a track which is designed to be connected to a source of electrical current. This track constitutes resistive means capable of emitting heat by resistive heating under the effect of the electrical current. This structuring can be achieved by virtue of an ionic chemical etching. Examples of this track will be described with reference to FIGS. 3 to 5.

When only the layer 45 is structured, the emissive layer 44 extends continuously over at least a part of the multilayer.

In one variant, the emissive layer 44 can also be structured like the resistive layer 45. Thus, the conducting track then rests on an emissive layer 44 with the same contour.

Lastly, a final protection layer 46 is deposited on the multilayer thus obtained, which completely coats the layers 44 and 45, deposited on a part of the interface layer 43.

This protection layer 46 can notably be formed from $SiO_2$ or $Si_3N_4$. As will be seen in the following part of the description, this layer has the function of protecting the device from thermal leaks and from oxidation. It could be omitted.

Generally speaking, the layers 40, 41, 42, 43, 44 and 46 are formed by conventional deposition techniques, for example a chemical vapor deposition (CVD in the English terminology), in which a plasma could potentially be employed (PECVD in the English terminology).

For the deposition of the resistive layer 45 of conducting material, a sputtering technique can be used.

A litho-etch step is carried out on the multilayer thus obtained, in such a manner as to obtain the waveguide 1 and, on the latter, the means of emission 2 of infrared radiation.

The waveguide then takes the form of a beam, supported by the layers 40 and 41, whose end carries the reference 12.

For a wavelength of 4 µm, the width of the waveguide will be in the range between 1.5 µm and several tens of microns, or even 100 µm. Its length will be typically of the order of a millimeter.

Figure 3:
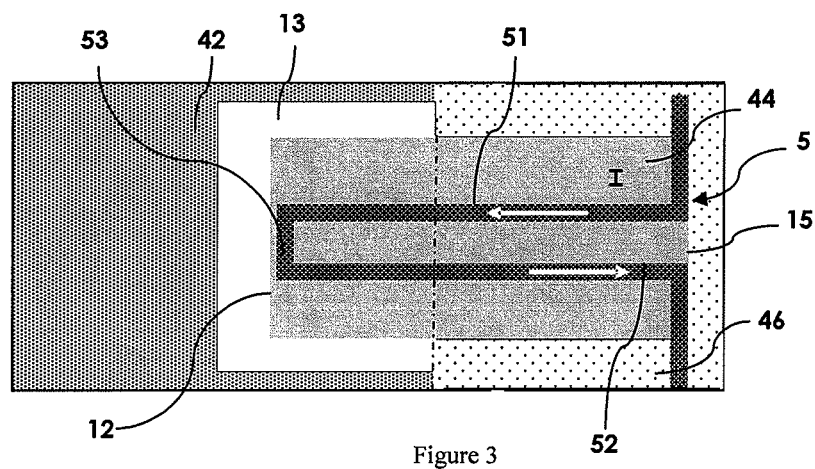
Figure 4:
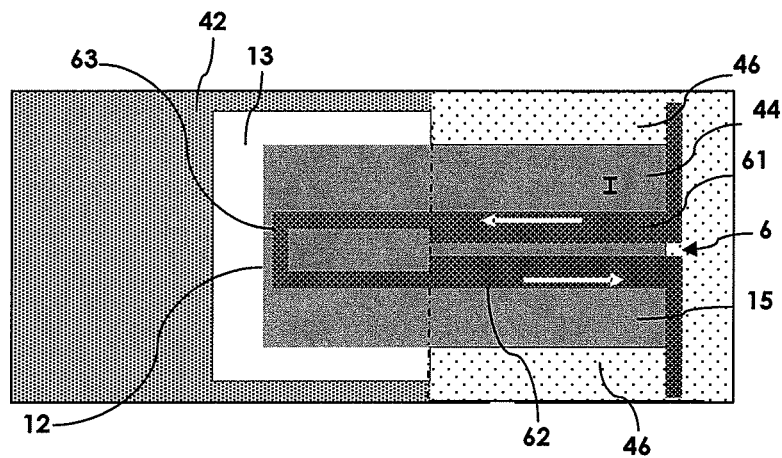
Figure 5:
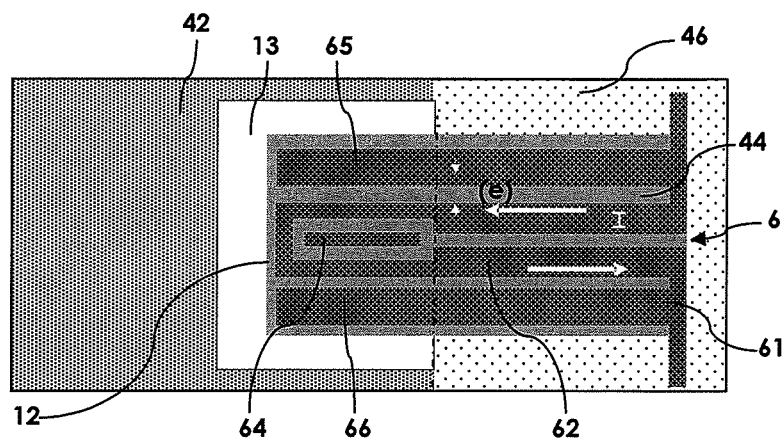

In the example illustrated in FIGS. 1 and 2, during this litho-etch step, the layers 41, 42, 43 and 46 are completely etched away in the region 47 bounded by the two dashed lines in FIG. 2. This region does not pass through the layers 44 and 45. The layers 41, 42, 43 and 46 have also been etched away on the longitudinal sides of the end part 11 of the guide, as is illustrated in FIGS. 3 to 5. A cavity 13 is thus formed around the waveguide.

In addition, another step is provided for eliminating a region of the layer 41 situated under the guide in order to obtain a cavity 10. This region 410 is bounded by two dashed lines in FIG. 2. This step is implemented, for example, by means of a high-frequency chemical etch process.

Thanks to these various steps, starting from the stack of the layers 40 to 46, the waveguide 1 is obtained on the two support layers 40 and 41. The means 2 for emitting infrared radiation comprising the layers 43 and 44, the conducting track obtained from the resistive layer 45 of conductive material and the protection layer 46 are formed on the guide.

It will thus be understood that the means 2 and the waveguide 1 are composed of a stack of layers some of which are structured.

Thus, the means 2 for emitting infrared radiation are in direct contact with the waveguide 1. This contact is made between the waveguide 1 and the interface layer 43 when the latter is provided, or otherwise, between the guide 1 and the emissive layer 44.

Thus, in the example illustrated in FIG. 2, a cavity 10 is provided under a part 11 of the waveguide. As will be seen in the following part of the description, this cavity is not necessary to the operation of the device according to the invention. Thus, the layer of silica 41 could be present under the entirety of the waveguide 1.

Reference is now made to FIGS. 3 to 5 which illustrate three examples of a conducting track formed from the layer 45 of conductive material.

All these figures are top views in the plane I-I in FIG. 1.

These figures illustrate the part of the guide on which the means for emitting infrared radiation are formed and which is situated near to its end.

This part of the waveguide is partially supported by the support layer 41. It comprises, going from the end 12 of the waveguide, the end part 11 then a part 14, illustrated in FIG. 1.

In the examples illustrated in FIGS. 3 to 5, the layer 41 has also been etched away under the part 11 of the waveguide closest to the end 12, as is illustrated in FIG. 1.

The cavity 10 thus formed communicates with the cavity 13 which is formed all around the end part 11 of the waveguide 1.

Thus, in the embodiment illustrated in the figures, the end of the waveguide is thermally insulated by virtue of the thermal insulator which is provided in the cavities 10 and 13. This thermal insulator can notably consist of air or a vacuum or else of any suitable material.

This allows the efficiency of the emission of the infrared radiation and its transmission to the waveguide to be improved.

The support layer 41 is still present under the part 14. Thus, the part of the waveguide on which the means 2 of emission are provided is free at its distal end 12 and held or supported at its opposite proximal end 15.

In the variant illustrated in FIG. 3, the resistive layer 45 of conductive material is structured in order to form a track 5 in the shape of a 'U' whose long branches 51 and 52 run substantially parallel to the longitudinal direction of the waveguide, these two branches being connected by a third branch 53 substantially parallel to the end 12 of the waveguide.

This track 5 is connected to an electrical current supply source which is not illustrated in FIG. 3.

In the variant illustrated in FIG. 3, the three branches of the track 5 have substantially the same width.

Figure 6:
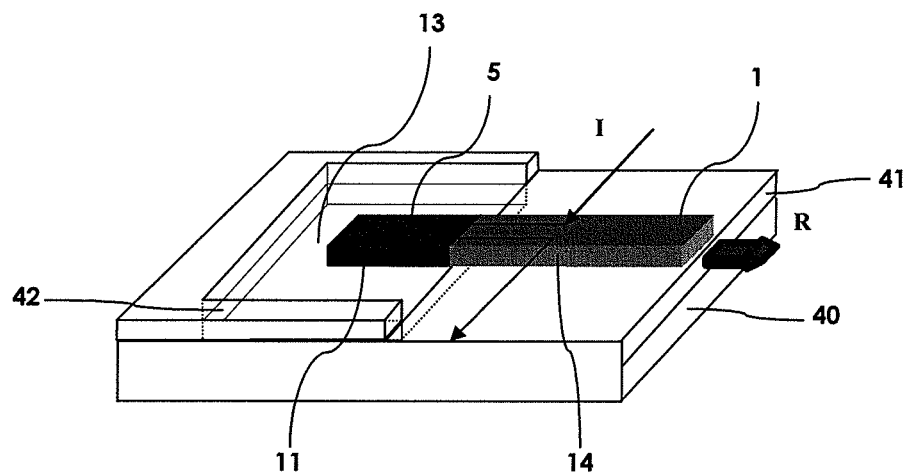
FIG. 6 is a simplified perspective view of the device according to the invention illustrating its operation.

The operation of the device illustrated in FIG. 3 will now be explained, with reference also to FIG. 6.

When a current I flows in the track 5, heat is generated by resistive heating. This heat diffuses into the emissive layer 44 formed from a material with a high thermal emissivity, which leads to a significant emission of infrared radiation. The latter is transmitted into the guide. This infrared radiation will subsequently be transported and guided, going from the part of the guide which is close to its end 12, toward the rest of the guide. The radiation transported by the guide 1 is symbolized by the arrow R in FIG. 6. It is confined within the waveguide.

Generally speaking, the waveguide is made of a material with a low absorption, in order to transport and guide the infrared radiation over its length. Thus, the waveguide intrinsically emits practically no infrared radiation.

In contrast, the materials deposited onto the guide, in particular that of the emissive layer 44, emit infrared radiation which is subsequently transmitted into the guide and transported by the latter.

In the various embodiments illustrated in the figures, the means for emitting infrared radiation within the guide all together comprise a conducting track, a layer 44 exhibiting a high thermal emissivity, an interface layer 43 and a protection layer 46.

The interface layer 43 promotes the coupling between the emissive layer 44 and the waveguide formed from the layer 42, and it therefore optimizes the transmission of the infrared radiation from the emissive layer 44 toward the waveguide 1.

The protection layer 46 protects the waveguide, together with the emissive layer 44 and resistive layer 45 of the emission means 2, both from thermal leaks and from oxidation.

However, these two interface 43 and protection 46 layers could be omitted.

FIG. 4 illustrates one variant embodiment of the conducting track, formed from the resistive layer 45 of electrically conductive material.

In the example of this embodiment, the conducting track 6 also has a U shape with two main branches 61 and 62 substantially parallel to the longitudinal direction of the waveguide and a branch 63 connecting them, being substantially parallel to the end 12 of the waveguide.

However, the width of the branches 61 and 62 is not constant, in contrast to the variant illustrated in FIG. 3. On the contrary, the width of the branches 61 and 62 is reduced in the part 11 of the waveguide situated on top of the cavity 10 with respect to the part 14 in contact with the support layer 41.

The variant illustrated in FIG. 4 allows the losses by resistive heating generated by the conducting track 6, when an electrical current is flowing through it, to be concentrated in the part 11 of the waveguide.

Thus, the heat energy emitted by resistive heating is concentrated in the part 11 of the guide which is, furthermore, more thermally isolated by virtue of the presence of a thermal insulator within the cavities 10 and 13. Thus, the emission of the infrared radiation is also generated in the part 11 of the guide then transmitted into the latter.

FIG. 5 illustrates a third variant embodiment, in which the conducting track is identical to the track 6 illustrated in FIG. 4.

On the other hand, the resistive layer 45 of an electrically conductive material has been structured so as to conserve, on the surface of the emissive layer 44, other regions of conductive material.

Thus, conductive material has been conserved between the two branches 61 and 62 of the track 6, in the part 11 of the guide, in which the thickness of these two branches is reduced.

This region of conductive material is identified by the reference 64.

Furthermore, conductive material is also present on the emissive layer 44, beyond the conducting track 6. This material thus forms two ribbons 65 and 66 which run in the longitudinal direction of the waveguide. These two ribbons are separated from the conducting track 6 by a free space having a thickness e.

The advantage of this variant embodiment is to promote the diffusion of the heat generated by the conducting track 6, in the whole of the part of the guide situated near to the distal end 12. In practice, the conductive material of the region 64 and of the ribbons 65 and 66 allows the heat generated by the track 6, when a current is flowing through it, to be diffused. The heating power remains however higher in the part 11.

Thus, the thickness e is chosen to be as thin as possible so as to optimize the thermal exchanges by conduction.

The invention is not limited to the embodiments which have been illustrated with reference to FIGS. 3 to 5. In particular, the track may also take the form of a serpentine or a double U.

As FIG. 1 illustrates, the device according to the invention can comprise a cover 3.

This cover can be obtained starting from a stack of two layers: a layer 30 for example of silica and a layer 31 of silicon nitride.

These two layers are partially eliminated, notably by means of a litho-etch process.

This allows a cavity 32 to be formed.

The cover 3 is placed on top of the multilayer in which the waveguide and the means 2 for emitting infrared radiation have been formed, in such a manner that the cavity 32 communicates with the cavity 13 formed around the waveguide and the emission means 2.

It can be fixed by adhesive bonding, notably by anodic or molecular bonding.

This cover 3 contributes to isolating the part 11 of the waveguide from the processes of oxidation or thermal exchanges.

It could also be formed from a substrate of silicon, hollowed out so as to also form a cavity.

When the cover is made of silicon, it can be fixed onto the protection layer 46 by means of a sealing process using molecular adherence under inert gas and with low thermal conductivity.

Figure 7:
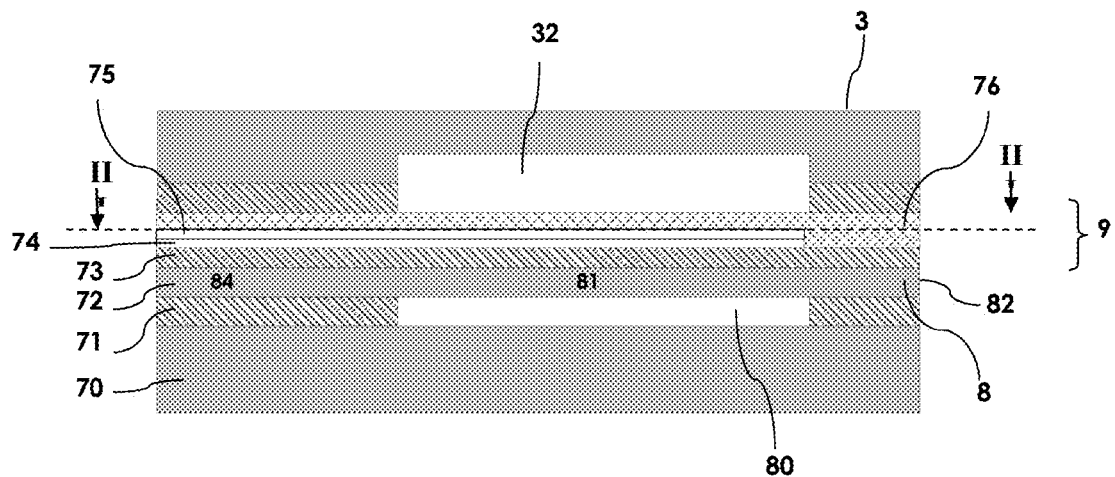
FIG. 7 is a transverse cross-sectional view of another exemplary embodiment of the device for emitting and for guiding infrared radiation according to the invention.
Figure 8:
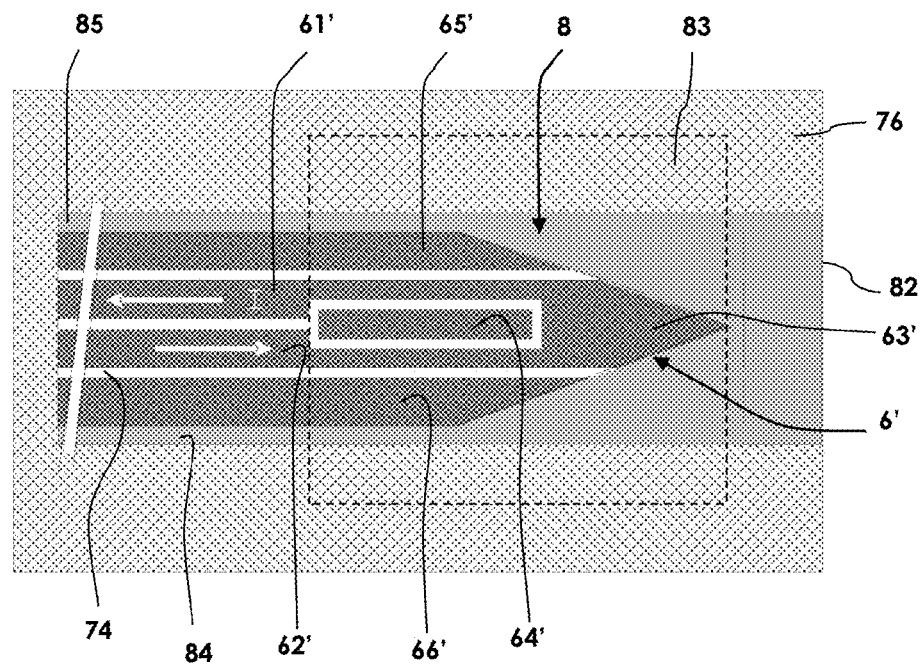
FIG. 8 is a top view, in the plane II-II, of the device illustrated in FIG. 7.

Reference is now made to FIGS. 7 and 8 which illustrate another exemplary embodiment of the device for emitting and for guiding infrared radiation according to the invention.

In this embodiment, the conducting track, formed from a layer of conductive material, is designed differently.

The device illustrated in these FIGS. 7 and 8 is again fabricated starting from a stack of several layers 70 to 76, which layers correspond to the layers 40 to 46 already described with reference to FIGS. 1 and 2.

The materials used to form the layers 40 to 46 may also be used to form the layers 70 to 76. Similarly, the same deposition techniques may be used.

Furthermore, the layers 70 to 76 fulfill the functions which have already been described for the layers 40 to 46.

Finally, the interface layer 73 and protection layer 76 are also optional layers. However, the efficiency of the device is increased when they are present.

As illustrated in FIG. 7, the emissive 74 and resistive 75 layers are only formed over a part of the multilayer.

Once this multilayer has been obtained, the structuring of the resistive layer 75 made from an electrically-conductive material is carried out. This structuring allows the conducting track 6' illustrated in FIG. 8 (which is a view in the plane II-II of FIG. 7) to be obtained.

This structuring may be obtained by means of an ionic chemical etch.

Furthermore, the track 8 is designed to be connected to a source of electrical current (not shown).

After structuring of the resistive layer 75, a final protection layer 76 is deposited which completely surrounds the emissive 74 and resistive 75 layers deposited on a part of the interface layer 73. Like the layer 46, the function of this protection layer 76 is to protect against thermal leaks and oxidation.

A litho-etch step is carried out on this stack of the layers 70 to 76 so as to obtain the waveguide 8 and, on the latter, the means of emission 9 of infrared radiation.

The waveguide, obtained starting from the layer 72, takes the form of a beam which is supported by the layers 70, 71.

On the part near to its end 82, the waveguide carries the means 9 for emitting infrared radiation, composed of the interface layer 73, of the emissive layer 74 of a material with high thermal emissivity, of the conducting track 6' and of the protection layer 76. In the example illustrated, the emissive layer 74 is located only under the conducting track obtained starting from the resistive layer 75.

This part of the waveguide comprises, going from the end 82, an end part 81 then a part 84.

In the exemplary embodiment illustrated in FIGS. 7 and 8, after the formation of the waveguide 8, another step is implemented so as to partially eliminate the layer of silica 71 under the part 81.

Thus, the layer of silica is eliminated on the longitudinal sides of the part 81. It is also partially eliminated under this same part 81.

A cavity 83 is thus formed on the sides of the part 81 and it communicates with the cavity 80 formed under the part 81. This part 81 is therefore liberated with respect to the layer 70.

In other words, the part of the waveguide on which the emission means 9 are formed is supported by the layer 71, at its distal end 82 and at its opposite proximal end 85.

As for the embodiment illustrated in FIGS. 1 and 2, the part 81 of the waveguide can be thermally insulated by virtue of a thermal insulator which is provided within the cavities 80 and 83.

Finally, as for the embodiment described with reference to FIG. 1, a cover 3 can be provided in order to close the cavity 83. This cover 3 will not be described again.

Reference is now again made to FIG. 8 in order to describe the conducting track 6' obtained from the resistive layer 75 of electrically-conductive material.

The track 6' is a variant of the track 6 illustrated in FIGS. 4 and 5.

Thus, the track 6' takes substantially the form of a 'U' with two main branches 61' and 62' substantially parallel to the longitudinal direction of the waveguide and a branch 63' connecting them.

The width of the branches 61' and 62' is thinner in the liberated part 81 of the waveguide than in the part 84 in contact with the support layer 71.

The effect of this, as has been explained with regard to FIG. 4, is to concentrate the heat energy, and hence the emission of the infrared radiation, within the part 81 of the waveguide which is the most thermally isolated, thanks to the presence of a thermal insulator within the cavities 80 and 83.

Furthermore, the part 63' which forms the base of the U does not take the form of a straight ribbon but takes the form of an arrow.

As illustrated in FIG. 5, in this embodiment, the resistive layer 75 of electrically-conductive material has been structured so as to conserve conductive material between the two branches 61' and 62', within the part 81 of the guide. This region is identified by the reference 64'.

Two strips of conductive material 65' and 66' are also present on the emissive layer 74, beyond the conducting track 6'.

These ribbons are separated from the conducting track 6' by a free space having a thickness e.

As explained with regard to FIG. 5, in the whole of the part of the guide situated near to its end 82, the conductive material provided outside of the is track 6' allows the diffusion of the heat generated by the conducting track 6' to be enhanced. However, in the embodiment illustrated, the heat energy, and hence the emission of the infrared radiation, is concentrated within the part 81.

FIG. 8 shows that the end of the ribbons 65' and 66' is beveled in such a manner as to be continuous with the part 63'.

Thus, it is the whole of the conductive material present on the emissive layer 74 which exhibits a tapered form in the direction of the distal end 82 of the waveguide.

This embodiment allows the transition between the part of the waveguide having the track 6' and that through which a current does not flow to be rendered more progressive.

This progressive character allows reflections at the transition between the two parts of the guide to be avoided. Indeed, these reflections are likely to reduce the infrared radiation transmitted into the waveguide.

Lastly, in this embodiment, the part of the waveguide having the means 9 of emission is supported both by its distal end and its proximal end.

This allows potential twist-inducing effects, which could occur in the waveguide during the process of fabrication of the waveguide and of the cavities 80 and 83, to be avoided.

In the exemplary embodiment illustrated in FIG. 8, the length of the part 81 within which the heat energy is concentrated can be in the range between 20 µm and 1 mm; it is typically 100 µm. These numerical values are also valid for the exemplary embodiments in FIGS. 3 to 5.

It is observed that, in all the embodiments that have been described, the means for emitting infrared radiation extend over at least a part of the waveguide, situated preferably at one end.

Furthermore, these means are in direct contact with the waveguide. In other words, no other layer or empty space exists between the means of emission of the infrared radiation and the waveguide.

Lastly, the means of emission of the infrared radiation and the waveguide form a stack of layers, some of which are structured.

The invention is not limited to the embodiments that have just been described.

In particular, the presence of an enclosure filled with a thermally insulating material allows the energy efficiency of the device according to the invention to be enhanced.

However, an acceptable energy efficiency would be obtained without this enclosure, notably by providing an interface layer with the waveguide that is thermally insulating. This may be obtained with a layer of silica or of ZnS—SiO$_2$ or, alternatively, of silicon nitride having a sufficient thickness, typically of a few microns and, in particular, greater than 1 μm. Furthermore, the waveguide could be supported in its entirety, without a cavity therefore being provided around a part of the waveguide.

In the various embodiments that have been described, the means for emitting infrared radiation are formed on the waveguide and more particularly on top of the waveguide.

These means could alternatively be formed on the waveguide but on the longitudinal sides of the latter.

Furthermore, they could also be provided inside of the waveguide. In this case, the layer of silicon 42 or 72, starting from which the waveguide is obtained, could be formed in two stages.

A first part of this layer would be deposited, the emission means would subsequently be formed before a second part of this layer of silicon is deposited.

Furthermore, a structuring could be provided on the waveguide, on the same side as the means for emitting infrared radiation but downstream of the latter, in the direction R of transport of the radiation.

This structuring could take the form of a photonic crystal structure or Bragg lattice, and could be used to promote the emission of infrared radiation in the direction R and to attenuate it in other directions.

Such structuring could also be used to implement a filtering along the waveguide. This is because the infrared radiation emitted by the emission means is a wideband radiation, and it could be useful to implement a filtering, downstream of the part of the waveguide in contact with the emission means, in order to extract a narrower spectrum.

Finally, the conducting tracks described with reference to FIGS. 3 to 5 and 8 may be connected to a current source, for example DC.

This source of electrical current could also be modulated so as to allow dynamic detection modes.

This can notably be advantageous when the device according to the invention is used in a particular application for detection of a gas.

Indeed, thanks to the presence of the emission means, the waveguide transports infrared radiation. This radiation is capable of exciting a gas present around the device according to the invention and notably a gas present downstream of the device, in the direction R.

The wavelength of the infrared radiation is then chosen to correspond substantially to the wavelength relating to an absorption line of the gas to be detected.

The detection technique used can notably be an absorption technique or a photo-acoustic technique.

With the absorption technique, the radiation transported by the waveguide must be made to interact with the gas. This can be done by locally interrupting the guide so that the light propagating within it interacts with the gas and is absorbed specifically at the wavelengths relating to an absorption line of the gas. This may also be done by locally thinning the guide so that light propagates around the guide and "sees" or "probes" the gas so as to be partially absorbed. This thinned region is typically situated outside of the housing covering the means for emitting infrared radiation.

The analysis of this absorption is done by any spectral analysis technique. The techniques operating on principles of guided optics (such as the SWIFT interferometer) are particularly well adapted.

With the photo-acoustic technique, the thinning of the guide and its liberation as a suspended structure is indicated. The part of the guide which is liberated is then different from that comprising the means for emitting infrared radiation. In this part of the guide both thinned and liberated from the substrate, a small amount of the light propagating within it is forced to exit from it so as to interact with the gas. Furthermore, the guide thus taking the form of a beam can vibrate by virtue of an excitation linked to the thermalization of the molecules of gas which are excited by the light. This excitation can be modulated for example by supplying the conducting track with current at intervals, so as to drive the vibration of the beam periodically and to thus increase the sensitivity of the method. The vibration of the guide in the form of a beam is detected by any known technique, such as a capacitive sensor in the neighborhood of the guide or piezo-electric effects, or even an optical effect if the beam is designed such that it comprises a liberated end, by detecting variations in intensity transmitted by the guide at its frequency of vibration.

The purpose of the reference numbers inserted after the technical features appearing in the claims is only intended to facilitate the understanding of the latter and will not limit their scope.

The invention claimed is:

1. A device for emitting and for guiding infrared radiation comprising a waveguide and means for emitting infrared radiation, wherein said means for emitting infrared radiation are in direct contact with the waveguide and comprise means of emission of heat in the form of a resistive track made from an electrically-conductive material, which is configured to be connected to an electrical current supply source; and means capable of emitting radiation under the effect of heat emitted by said resistive track, said means of emitting radiation being in the form of an emissive layer made of a material capable of emitting infrared radiation under the effect of heat, said emissive layer being placed between the waveguide and the resistive track.

2. The device as claimed in claim 1, wherein the means for emitting infrared radiation are in direct contact with the waveguide.

3. The device as claimed in claim 1, wherein the waveguide is thermally insulated by air or a vacuum.

4. The device as claimed in claim 1, wherein the means for emitting infrared radiation comprise an interface layer in contact with the waveguide.

5. The device as claimed in claim 1, wherein the means for emitting infrared radiation extend over or within at least a part of the waveguide.

6. The device as claimed in claim 5, wherein said part of the waveguide this part is supported at its proximal end, its distal end being free.

7. The device as claimed in claim 5, wherein the proximal end and distal end of said part are supported, a cavity being formed between these two ends.

8. The device as claimed in claim 6, wherein said resistive track has a width that is narrower near to the distal end of said part than in the rest of the waveguide.

9. The device as claimed in claim 8, wherein said resistive track exhibits a tapered shape in the direction of this distal end.

10. A gas detector comprising a device for emitting and for guiding infrared radiation as claimed in claim 1.

* * * * *